US008808691B2

(12) United States Patent
Armbruster et al.

(10) Patent No.: US 8,808,691 B2
(45) Date of Patent: Aug. 19, 2014

(54) METHOD FOR TREATING TUMORS AND THEIR METASTASES

(75) Inventors: Franz Paul Armbruster, Bensheim (DE); Markus Karmatschek, Bensheim (DE); Franz Werner Nader, Bensheim (DE); Ulf Joerg Forssmann, Hannover (DE); Mats Paulsson, Cologne (DE); Martin R. Berger, Cologne (DE)

(73) Assignee: Armbruster Biotechnology GmbH, Bensheim (DE)

( * ) Notice: Subject to any disclaimer, the term of this patent is extended or adjusted under 35 U.S.C. 154(b) by 884 days.

(21) Appl. No.: 12/901,399

(22) Filed: Oct. 8, 2010

(65) Prior Publication Data
US 2011/0091379 A1 Apr. 21, 2011

Related U.S. Application Data

(62) Division of application No. 10/480,465, filed as application No. PCT/EP02/06456 on Jun. 12, 2002, now Pat. No. 7,825,219.

(30) Foreign Application Priority Data

Jun. 13, 2001 (EP) ..................................... 01114388
Jun. 15, 2001 (DE) ................................. 101 28 639

(51) Int. Cl.
*A61K 39/395* (2006.01)
(52) U.S. Cl.
USPC ..................................... 424/130.1; 424/277.1
(58) Field of Classification Search
None
See application file for complete search history.

(56) References Cited

U.S. PATENT DOCUMENTS

| 4,853,219 | A | 8/1989 | Alderman et al. |
| 5,340,934 | A | 8/1994 | Termine et al. |
| 5,601,819 | A | 2/1997 | Wong et al. |
| 6,407,213 | B1 | 6/2002 | Carter et al. |

FOREIGN PATENT DOCUMENTS

WO WO-0062065 A1 10/2000

OTHER PUBLICATIONS

Tuck et al Oncogenes 18:4237-46, 1999.*
Diel et al, Clinical Cancer Research, 5:3914-3919, 1999.*
Diel et al,New Engl J Med, 339:357-3.*
Tsurushita et al, Immuno Meth, vol. 295, p. 9-19, 2004.
Kamihira et al, J of Virology, vol. 79, p. 10864-74, 2005.
Mesh word search in NLBI for complement factor H, Jun. 2009.
Diel et al., Clinical Cancer Res. vol. 5, p. 3914-3919, 1999.
Wuttke et al., J Biol Chem. vol. 276, p. 36839-36848, 2001.
Fedarko et al., Journal of Biological Chemistry, vol. 275, No. 22, pp. 16666-16672 (2000).
Fisher et al., Acta Orthopaedica Scandinavica, vol. 66, No. Suppl. 266, pp. 61-65 (1995).
Withold et al., Clinical Chemistry, vol. 43, No. 1, pp. 85-91 (1997).
Amizuka et at., Endocrinology, 137 :5055-67, 1996.
Ouyang et al., Endocrinology, 141: 4671-4680, 2000.
Camenisch et al., FASEB, vol. 13, p. 81-88, 1999.
Sequence search of database NCBI, Accession No. P21815, published May 1, 1991.

* cited by examiner

*Primary Examiner* — Lei Yao
(74) *Attorney, Agent, or Firm* — Birch, Stewart, Kolasch & Birch, LLP

(57) ABSTRACT

The invention relates to a method of therapy against tumors and their metastases, which preferentially settle in bone tissue, comprising administering to a patient in need thereof an active ingredient which comprises at least one binding molecule that binds to human bone sialoprotein or a fragment thereof.

10 Claims, 13 Drawing Sheets

Phe-Ser-Met-Lys-Asn-Leu-His-Arg-Arg-Val$^{10}$-Lys-Ile-Glu-Asp-Ser-
Glu-Glu-Asn-Gly-Val$^{20}$-Phe-Lys-Tyr-Arg-Pro-Arg-Tyr-Tyr-Leu-Tyr$^{30}$-
Lys-His-Ala-Tyr-Phe-Tyr-Pro-His-Leu-Lys$^{40}$-Arg-Phe-Pro-Val-Gln-
Gly-Ser-Ser-Asp-Ser$^{50}$-Ser-Glu-Glu-Asn-Gly-Asp-Asp-Ser-Ser-Glu$^{60}$-
Glu-Glu-Glu-Glu-Glu-Glu-Thr-Ser-Asn$^{70}$-Glu-Gly-Glu-Asn-Asn-
Glu-Glu-Ser-Asn-Glu$^{80}$-Asp-Glu-Asp-Ser-Glu-Ala-Glu-Asn-Thr-Thr$^{90}$-
Leu-Ser-Ala-Thr-Thr-Leu-Gly-Tyr-Gly-Glu$^{100}$-Asp-Ala-Thr-Pro-Gly-
Thr-Gly-Tyr-Thr-Gly$^{110}$-Leu-Ala-Ala-Ile-Gln-Leu-Pro-Lys-Lys-Ala$^{120}$-
Gly-Asp-Ile-Thr-Asn-Lys-Ala-Thr-Lys-Glu$^{130}$-Lys-Glu-Ser-Asp-Glu-
Glu-Glu-Glu-Glu$^{140}$-Glu-Glu-Gly-Asn-Glu-Asn-Glu-Glu-Ser-Glu$^{150}$-
Ala-Glu-Val-Asp-Glu-Asn-Glu-Gln-Gly-Ile$^{160}$-Asn-Gly-Thr-Ser-Thr-
Asn-Ser-Thr-Glu-Ala$^{170}$-Glu-Asn-Gly-Asn-Gly-Ser-Ser-Gly-Gly-Asp$^{180}$-
Asn-Gly-Glu-Glu-Gly-Glu-Glu-Glu-Ser-Val$^{190}$-Thr-Gly-Ala-Asn-Ala-
Glu-Gly-Thr-Thr-Glu$^{200}$-Thr-Gly-Gly-Gln-Gly-Lys-Gly-Thr-Ser-Lys$^{210}$-
Thr-Thr-Thr-Ser-Pro-Asn-Gly-Gly-Phe-Glu$^{220}$-Pro-Thr-Thr-Pro-Pro-
Gln-Val-Tyr-Arg-Thr$^{230}$-Thr-Ser-Pro-Pro-Phe-Gly-Lys-Thr-Thr-Thr$^{240}$-
Val-Glu-Tyr-Glu-Gly-Glu-Tyr-Glu-Tyr-Thr$^{250}$-Gly-Val-Asn-Glu-Tyr-
Asp-Asn-Gly-Tyr-Glu$^{260}$-Ile-Tyr-Glu-Ser-Glu-Asn-Gly-Glu-Pro-Arg-
Gly-Asp-Asn-Tyr-Arg-Ala-Tyr-Glu-Asp-Glu$^{280}$-Tyr-Ser-Tyr-Phe-Lys-
Gly-Gln-Gly-Tyr-Asp$^{290}$-Gly-Tyr-Asp-Gly-Gln-Asn-Tyr-Tyr-His-His$^{300}$-
Gln

Fig. 3

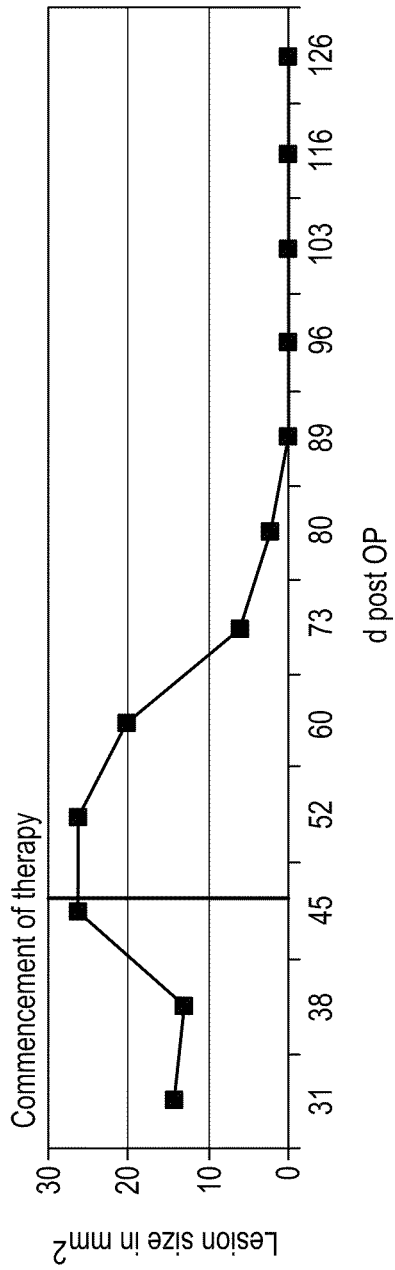

SEQUENCE LISTING

```
<160> NUMBER OF SEQ ID NOS: 18

<210> SEQ ID NO 1
<211> LENGTH: 15
<212> TYPE: PRT
<213> ORGANISM: Homo sapiens

<400> SEQUENCE: 1

Tyr Thr Gly Leu Ala Ala Ile Gln Leu Pro Lys Lys Ala Gly Asp
1               5                   10                  15

<210> SEQ ID NO 2
<211> LENGTH: 301
<212> TYPE: PRT
<213> ORGANISM: Homo sapiens

<400> SEQUENCE: 2

Phe Ser Met Lys Asn Leu His Arg Arg Val Lys Ile Glu Asp Ser Glu
1               5                   10                  15

Glu Asn Gly Val Phe Lys Tyr Arg Pro Arg Tyr Tyr Leu Tyr Lys His
                20                  25                  30

Ala Tyr Phe Tyr Pro His Leu Lys Arg Phe Pro Val Gln Gly Ser Ser
            35                  40                  45

Asp Ser Ser Glu Glu Asp Gly Asp Asp Ser Ser Glu Glu Glu Glu Glu
        50                  55                  60

Glu Glu Glu Thr Ser Asn Glu Gly Glu Asn Asn Glu Glu Ser Asn Glu
65                  70                  75                  80

Asp Glu Asp Ser Glu Ala Glu Asn Thr Thr Leu Ser Ala Thr Thr Leu
                85                  90                  95

Gly Tyr Gly Glu Asp Ala Thr Pro Gly Thr Gly Tyr Thr Gly Leu Ala
                100                 105                 110

Ala Ile Gln Leu Pro Lys Lys Ala Gly Asp Ile Thr Asn Lys Ala Thr
            115                 120                 125

Lys Glu Lys Glu Ser Asp Glu Glu Glu Glu Glu Glu Glu Glu Gly Asp
        130                 135                 140

Glu Asn Glu Glu Ser Glu Ala Glu Val Asp Glu Asp Glu Gln Gly Ile
145                 150                 155                 160

Asn Gly Thr Ser Thr Asn Ser Thr Glu Ala Glu Asn Gly Asn Gly Ser
                165                 170                 175

Ser Gly Gly Asp Asn Gly Glu Glu Gly Glu Glu Glu Ser Val Thr Gly
            180                 185                 190

Ala Asn Ala Glu Gly Thr Thr Glu Thr Gly Gly Gln Gly Lys Gly Thr
        195                 200                 205

Ser Lys Thr Thr Thr Ser Pro Asn Gly Gly Phe Glu Pro Thr Thr Pro
    210                 215                 220

Pro Gln Val Tyr Arg Thr Thr Ser Pro Pro Phe Gly Lys Thr Thr Thr
225                 230                 235                 240
```

```
Val Glu Tyr Glu Gly Glu Tyr Glu Tyr Thr Gly Val Asn Glu Tyr Asp
                245                 250                 255

Asn Gly Tyr Glu Ile Tyr Glu Ser Glu Asn Glu Pro Arg Gly Asp
        260                 265                 270

Asn Tyr Arg Ala Tyr Glu Asp Glu Tyr Ser Tyr Phe Lys Gly Gln Gly
        275                 280                 285

Tyr Asp Gly Tyr Asp Gly Gln Asn Tyr His His Gln
        290                 295                 300

<210> SEQ ID NO 3
<211> LENGTH: 12
<212> TYPE: PRT
<213> ORGANISM: Homo sapiens

<400> SEQUENCE: 3

Leu Gly Tyr Gly Glu Asp Ala Thr Pro Gly Thr Gly
1               5                   10

<210> SEQ ID NO 4
<211> LENGTH: 12
<212> TYPE: PRT
<213> ORGANISM: Homo sapiens

<400> SEQUENCE: 4

Glu Thr Gly Gly Gln Gly Lys Gly Thr Ser Lys Thr
1               5                   10

<210> SEQ ID NO 5
<211> LENGTH: 12
<212> TYPE: PRT
<213> ORGANISM: Homo sapiens

<400> SEQUENCE: 5

Phe Lys Gly Gln Gly Tyr Asp Gly Tyr Asp Gly Gln
1               5                   10

<210> SEQ ID NO 6
<211> LENGTH: 15
<212> TYPE: PRT
<213> ORGANISM: Homo sapiens

<400> SEQUENCE: 6

Ile Gln Leu Pro Lys Lys Ala Gly Asp Ile Thr Asn Lys Ala Thr
1               5                   10                  15

<210> SEQ ID NO 7
<211> LENGTH: 15
<212> TYPE: PRT
<213> ORGANISM: Homo sapiens

<400> SEQUENCE: 7

Tyr Thr Gly Leu Ala Ala Ile Gln Leu Pro Lys Lys Ala Gly Asp
1               5                   10                  15

<210> SEQ ID NO 8
<211> LENGTH: 17
<212> TYPE: PRT
<213> ORGANISM: Homo sapiens

<400> SEQUENCE: 8

Gly Asp Ile Thr Asn Lys Ala Thr Lys Glu Lys Glu Lys Glu Ser Asp
1               5                   10                  15

Glu
```

```
<210> SEQ ID NO 9
<211> LENGTH: 38
<212> TYPE: PRT
<213> ORGANISM: Homo sapiens

<400> SEQUENCE: 9

Ser Glu Asn Gly Glu Pro Asp Gly Asp Asn Tyr Arg Ala Tyr Glu Asp
1               5                   10                  15
Glu Tyr Ser Tyr Phe Lys Gly Gln Gly Tyr Asp Gly Tyr Asp Gly Gln
            20                  25                  30
Asn Tyr Tyr His His Gln
        35

<210> SEQ ID NO 10
<211> LENGTH: 15
<212> TYPE: PRT
<213> ORGANISM: Homo sapiens

<400> SEQUENCE: 10

Tyr Thr Gly Leu Ala Ala Ile Gln Leu Pro Lys Lys Ala Gly Asp
1               5                   10                  15

<210> SEQ ID NO 11
<211> LENGTH: 18
<212> TYPE: PRT
<213> ORGANISM: Homo sapiens

<400> SEQUENCE: 11

Tyr Glu Ser Glu Asn Gly Glu Pro Arg Gly Asp Asn Tyr Arg Ala Tyr
1               5                   10                  15
Glu Asp

<210> SEQ ID NO 12
<211> LENGTH: 9
<212> TYPE: PRT
<213> ORGANISM: Homo sapiens

<400> SEQUENCE: 12

Leu Lys Arg Phe Pro Val Gln Gly Gly
1               5

<210> SEQ ID NO 13
<211> LENGTH: 34
<212> TYPE: DNA
<213> ORGANISM: Homo sapiens

<400> SEQUENCE: 13
gcccgctagc cttctcaatg aaaaatttgc atcg                            34

<210> SEQ ID NO 14
<211> LENGTH: 38
<212> TYPE: DNA
<213> ORGANISM: Homo sapiens

<400> SEQUENCE: 14
caatgactgc ggccgctcac tggtggtggt agtaattc                        38

<210> SEQ ID NO 15
<211> LENGTH: 5
<212> TYPE: PRT
<213> ORGANISM: Homo sapiens
```

```
<400> SEQUENCE: 15

Thr Gly Leu Ala Ala
1               5

<210> SEQ ID NO 16
<211> LENGTH: 6
<212> TYPE: PRT
<213> ORGANISM: Homo sapiens

<400> SEQUENCE: 16

Tyr Thr Gly Leu Ala Ala
1               5

<210> SEQ ID NO 17
<211> LENGTH: 6
<212> TYPE: PRT
<213> ORGANISM: Homo sapiens

<400> SEQUENCE: 17

Tyr Thr Leu Pro Ala Ala
1               5

<210> SEQ ID NO 18
<211> LENGTH: 7
<212> TYPE: PRT
<213> ORGANISM: Homo sapiens

<400> SEQUENCE: 18

Asp Ala Thr Pro Gly Thr Gly
1               5
```

US 8,808,691 B2

METHOD FOR TREATING TUMORS AND THEIR METASTASES

This application is a Divisional of U.S. patent application Ser. No. 10/480,465 file May 19, 2004, U.S. Pat. No. 7,825,219, which is the National Stage of International Application PCT/EP02/06456 filed on Jun. 12, 2002, to which priority is claimed under 35 U.S.C. §120, which in turn claims priority to both of European Application 01114388.0, filed on Jun. 13, 2001 and German Application 10128639.2, filed on Jun. 15, 2001, under 35 U.S.C. §119.

FIELD OF THE INVENTION

The invention relates to methods for the treatment and combating of tumors and of metastases, which particularly frequently settle in bony tissue.

BACKGROUND OF THE INVENTION

At the present time many medicaments are in development which are intended to combat tumors and their metastases which spread in bone. Despite all advances in medicaments, bone metastases, however, do not count as being curable or treatable. There are attempts, by means of antibodies against surface antigens of tumor cells, to combat their metastases. Bone metastases are, however, despite this the cause of death in 73% of cases of tumors of the breast, and 68% of cases for tumors of the prostate gland. For tumors of other tissues the following figures apply: cervix 50%, thyroid gland 42%, bladder 40%, lungs 36%, ovaries 9% and colon 6%.

Tumor cells which express the so-called bone sialoprotein have the peculiarity that they prefer to settle in bony tissue and form metastases there, particularly in the case of tumors of the prostate gland, breast, lungs, kidney and thyroid and less frequently in the case of malign and semi-malign tumors. The bone sialoprotein (BSP) is a phosphorylated bone glycoprotein having a relative mass of ca. 80 kDa in the SDS-PAGE. The cDNA for BSP codes for a peptide sequence of ca. 33 kDa (Fisher L. W. et al. (1990), J. Biol. Chem. 265, 2347-51; U.S. Pat. No. 5,340,934). BSP is one the few matrix proteins the occurrence of which on mineralising tissue such as bones, dentin and calcifying cartilage is restricted. BSP represents ca. 10 to 15% if the total non-collagenic proteins in the bone matrix. It is as a rule expressed by cells which take part in the formation of dentin, bones and cartilage, for example osteoblasts, developing osteocytes, hypertrophic chondrocytes, odontoblasts and cementoblasts, but also by the trophoblasts in the placenta and some types of cancer cells, e.g. in the case of lungs, breast, prostate, kidney, thyroid and neuroblastoma primary and secondary tumors, in the case of multiple myeloma and in bone metastases. The degree of expression of BSP by the tumor closely correlates with the severity of the cancer (Waltregny D. et al., *Increased expression of bone sialoprotein in bone metastases compared with visceral metastases in human breast and prostate cancers*, in J. Bone Miner. Res., 2000, 15(5), 834-43; Bellahcéne, A. et al., *Bone sialoprotein expression in primary human breast cancer is associated with bone metastases development*, in J. Bone Miner. Res., 1996, 11, 665-670; Waltregny, D. et al., *Prognostic value of bone sialoprotein expression in clinically localised human prostate cancer*, in Journal of the National Cancer Institute, 1998, 90, 1000-1008; Bellahcéne, A. et al., *Expression of bone sialoprotein in primary breast cancer is associated with poor survival*, in Int, J. Cancer, 1996, 69, 350-353).

BSP, as an adhesion molecule, is supposed to bring about attachment and dissemination of cells on the tissue matrix, since in vitro it forms crystallisation nuclei for biological apatite and in vivo takes part in mineralisation. The switching off of the BSP gene in knock-out mice leads to no recognisable disruption of the building and functioning of the skeleton. In tumors BSP is attributed with participation in microcalcification (Castronovo, V. et al., *Evidence that breast cancer associated microcalcifications are mineralized malignant cells*, in Int. J. Oncol., 1998, 12, 305-308) and the colonisation of bones by metastasising tumor cells (Bellahcéne, A. et al., *Expression of bone sioloprotein in primary breast cancer is associated with poor survival*, in Int. J. Cancer, 1996, 69, 350-353).

The level of concentration of BSP in the serum of patients with primary carcinomas serves for diagnosis of whether these patients have bone metastases or such are likely to arise from the primary tumor (Diploma Thesis of Ms. Ina-Alexandra Meier, Development of a radioimmunoassay for the determination of bone sialoprotein (BSP) ["*Entwicklung eines Radioimmunoassays zur Bestimmung von Bonesialoprotein (BSP)*]", 1996, Darmstadt, Technical University [Fachhochschule], Specialist Field Chemical Technology [FB Chemische Technologie]; Dissertation of Mr. Markus Karmatschek, Isolation of bone sialoprotein from human bones, Structure of a radioimmunoassay for the measurement thereof in serum ["*Isolierung von Bonesialoprotein aus humanem Knochen, Aufbau eines Radioimmunoassays zur dessen Messung im Serum*"], 1996; Specialist Field of Biology of the Technical University of Darmstadt [FB Biologie der Technischen Hochschule Darmstadt]; Diel I. J. et al., *Elevated bone sialoprotein in primary breast cancer patients is a potent marker for bone metastases*; in Proceedings of ASCO, 1998, 17, Abstract 461; Diel I. J. et al, *Serum bone sialoprotein in patients with primary breast cancer is a prognostic marker for subsequent bone metastasis*, in Clin. Cancer Res., 1999, 5, 3914-19; DE 198 13 633; DE 198 21 533; WO 99/50666).

However, in body fluids free BSP is bound by complement factor H with high affinity. Further, BSP can bind to various receptors. Thus, there have been produced in rabbits antibodies against various peptide partial structures of BSP (Fisher, L. W. et al., *Antisera and cDNA probes to human and certain animal model bone matrix noncollagenous proteins*. Acta Orthop Scand Suppl., 1995, 266, 61-655), against recombinant BSP (Stubbs J T 3$^{rd}$ et al., *Characterization of native and recombinant bone sialoprotein: delineation of the mineral-binding and cell adhesion domains and structural analysis of the RGD domain*. J. Bone Miner. Res. 1997 12(8), 1210-22), and against BSP isolated from bones, which antibodies failed to recognise any BSP in human serum. The larger factor H molecule of 150 kDa probably masks the smaller BSP (of ca. 65 kDa), so that antibodies cannot bind. Further, factor H is present in excess in the serum (0.5 mg factor H/mL in comparison to BSP with <20 ng/ml Serum in the case of healthy persons and max. 160 ng/ml in the case of tumor patients). It has been asserted that immunological direct determination of BSP in body fluids is impossible, without reducing sample preparation, due to the binding to the factor H and possibly that trophoblasts and BSP producing tumor cells are thereby protected from attack by the immune system, since the factor H belongs to the complement system and is known to bring about a restriction of the alternative pathway to complement lysis (Fedarko N. S. et al., *Factor H binding of bone sialoprotein and osteopontin enables tumor cell evasion of complement-mediated attack*, in J. Biol. Chem., 200, 275, 16666-16672; WO 00/062065). Further, BSP can specifically bind to the integrin receptors on the cell surface through its own recognition sequence (arginine-glycine-aspartate, RGD). In the case of expression of BSP the tumor cells are then supposed to bind the factor H in the blood and in the tissue fluids to their cell surfaces, or concentrate it around them. Such a protection of BSP from the complement system of the blood of the mother is suspected also for the trophoblasts in the placenta (Fedarko N. S. et al. *Factor H binding of bone sialoprotein and osteopontin enables tumor cells evasion of complement-mediated attack*, in J. Biol. Chem., 200, 275, 16666-16672; WO 00/062065). Further there is also suspected a function of BSP in angiogenesis. Along with the adhesion of osteoclasts and osteoblasts to the bone matrix—through the binding of the RGD recognition sequence in the matrix to the alpha(v)beta(3) integrin receptors on the cell wall—it is also observed that the adhesion, dissemination and orientation of the endothelial cells is probably mediated by BSP. Namely, blood vessel formation around a tumor occurs in parallel with the BSP expression in the tumor cells (Bellahcène A et al., *Bone sialoprotein mediates human endothelial cell attachment and migration and promotes angiogenesis*, in Circ. Res. 2000, 86(8), 885-91).

These characteristics thus make BSP a starting point for medicaments of all kinds. Thus, the binding of BSP via the RGD sequence to vitronectin or integrin receptors of tumor and epithelial cells can be restricted by antagonists (U.S. Pat. No. 6,069,158; U.S. Pat. No. 6,008,213; U.S. Pat. No. 5,849,865; van der Pluijm et al., *Bone Sialoprotein peptides are potent inhibitors of breast cancer cell adhesion to bone in vitro*, in Cancer Res., 1996, 56, 1948-1955). EP 1 084 719 A1 teaches a pharmaceutical composition having BSP as active substance for the support of the repair of damaged bone and connective tissue. WO 94/13310 teaches a composition having a BSP binding protein of *Staphylococcus aureaus* as active ingredient. WO 00/36919 discloses regulatory elements for the purposive monitoring and suppression of the expression of BSP in tumor and connective tissue cells, which promote calcification. Thus, generally the substances of the regulation of the cell growth and cell migration are of particular interest from a diagnostic and therapeutic point of view. There are, however, still very many unknown factors which control cancer growth, whereby primary and secondary tumors and colonised organs interact. Here, important steps are the invasion, adhesion, migration and cell division of the tumor cells. Along with matrix metalloproteinases, adhesion molecules and chemotactic factors play a particular role. A medicament for combating and also for healing bone metastases on the basis of antibodies and binding molecules against BSP is not known. It is also not known that the BSP of tumor cells is different from the BSP of normal healthy cells.

SUMMARY OF THE INVENTION

The subject of the invention is a method for therapy of tumors and their metastases, which preferentially settle in bony tissues, including as active ingredient at least one binding molecule which binds to bone sialoprotein. The active ingredient comprises a binding molecule which binds to a bone sialoprotein modified in its glycosylation. The binding molecule may be an antibody or an aptamer which specifically binds bone sialoprotein from tumor cells. The binding molecule binds to or it can be produced against bone sialoprotein from bone material, which is modified chemically or naturally in its glycosylation, the donor of which was not capable of normal glycosylation of bone proteins.

In a particularly preferred embodiment, the active ingredient comprises an antibody or a plurality of antibodies against human bone sialoprotein (hBSP), which bind epitopes present on human sialoprotein from tumor cells, the post-translational glycosylation of which is modified or incomplete, in comparison with normal bone sialoprotein from bones, in the region of the amino acids 108 to 122 of SEQ ID NO:2 (=amino acids 120 to 135 of SWISSPROT: SIAL_HUMAN, Acc. No. P21815, incl. signal sequence) containing the amino acids TGLAA (SEQ ID NO:15) or YTGLAA (SEQ ID NO:16). The method of therapy in accordance with the invention may also comprises the administration of an active ingredient comprising an antibody and/or an aptamer produced against a hBSP epitope, including the amino acid sequence TGLAA (SEQ ID NO:15) or YTGLAA (SEQ ID NO:16) and optionally sugar groups. The active ingredient may comprise a chicken IgY antibody. The chicken IgY antibody may also be a corresponding human or humanised antibody. Further preferred are medicaments whereby the binding molecule contains as a bispecific antibody also an additional paratope which is preferably specific for epitopes of CD3. The active ingredient may also be an immunotoxin that is a conjugate of binding molecule and a residue having cytotoxic activity. The immunotoxin may for example be a conjugate which contains the ricin-A-chain or a non-binding fragment of the diphtheria toxin. The binding molecule may, further, be coupled with a radionuclide so that the medicament can also be put to use for immune scintigraphy or for the localisation and observation of development of bone metastases.

The medicament in accordance with the invention may also contain at least one antibody, ligand or inhibitor, from the group comprising adhesion molecules, membrane associated proteases, receptors which mediate chemotaxis, chemokine receptors, apoptosis inducing substances. The inhibitors can be so selected that they at least partially block BSP and modulate its function. In terms of its range of applications, the medicament in accordance with the invention is thus particularly suitable for the treatment of tumors from the group comprising prostate, breast, lung, kidney and thyroid tumors, tumor diseases of the blood system, of the lymphatic system, and of the heart and circulatory system, the nervous system, the respiratory tract, the digestive tract, the endocrinic system, the skin including adnexa, the locomotory system and of the urogenital tract.

There will now be described further features and advantages of the invention with reference to the examples and the accompanying drawings.

BRIEF DESCRIPTION OF THE DRAWINGS

There is shown:

FIG. 3 the amino acid sequence of secreted BSP (SEQ ID No. 2) according to Fisher et al. (1991);

FIG. 5a curve of lesion size, in square millimeters, of a bone metastasis on the distal femur of rat 987 over the period of observation and therapy;

DETAILED DESCRIPTION OF THE INVENTION

Figure 1:
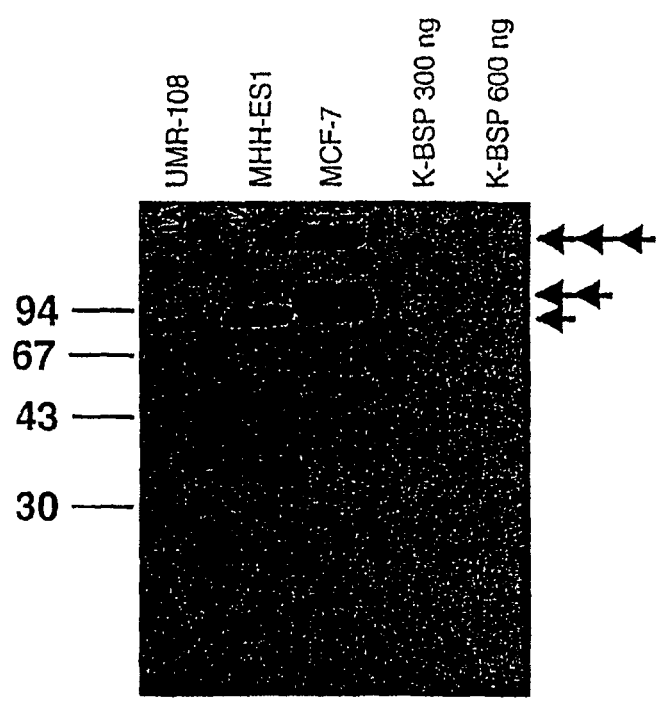
FIG. 1 a Western Blot with tumor and bone specific isoforms of BSP.

The subject of the invention is thus a method for the therapy of tumor diseases, which contains as active ingredient a BSP specific binder molecule such as an antibody, ligand or inhibitor. In one embodiment, the binder molecule is an antibody or an aptamer on the basis of RNA or DNA which recognises BSP in the presence of factor H. Particularly preferred binder molecules recognise specifically BSP from tumor cells. The medicament can be reinforced with the following substances: antibodies, ligands or inhibitors which interact with adhesion molecules, with membrane-associated proteases, or with receptors which mediate chemotaxis such as for example the chemokine receptors, and apotosis inducing substances such as preferably antibodies, aptamers or proteins/peptides which are obtained from natural or artificial peptide banks. A specific protein (peptide) interaction preferably with non-specific molecules which are obtained from natural extracts, from synthetically or recombinantly produced binding proteins, and from other peptide/protein banks, is however not sufficient to bring about the effect of apoptosis of tumor cells. After appropriate diagnosis, a specific therapy can be applied. Here, surprisingly, with the use of anti-BSP antibodies or binding proteins there is observed an accelerated occurrence of tumor cell death (apoptosis).

In particular, tumors which can be treated in this way are of the group including breast, prostate, lung, kidney and thyroid tumors, and tumors of the blood system, of the lymphatic system, of the heart and circulatory system, of the nervous system, of the respiratory tract, of the digestive tract, of the endocrine system, the skin including adnexa, of the locomotory system, and of the urogenital tract including the kidneys.

The administering of the binding proteins and antibodies allows a new therapy of tumor diseases on the basis of the BSP system and strengthening with the inclusion of further tumor surface-associated proteome clusters. The medicament is based on the employment of BSP-specific antibodies, aptamers, ligands or inhibitors against the primary or secondary tumor and dispersing metastases; that is, for the suppression of cancer growth, inclusive of metastasisation. The medicament in accordance with the invention is based on the determination that BSP acts, through autocrinic, paracrinic and endocrinic paths, via the disease specific constellation of the tumor cell proteomes on specific tumor cells. Primary and certain secondary tumors are controlled in their adhesion, migration and proliferation behaviour. Through diagnostic determination of the locally increased expressed and regulated factors, and the presence of BSP, there is provided the possibility of decisively suppressing or completely preventing cancer growth, including tumor metastasation.

A further embodiment of the invention relates to the employment of the antibodies in accordance with the invention in pharmaceutical compositions for the treatment of tumors and metastases. The antibodies in accordance with the invention, and their part structures or conjugates, can be applied through injection or via suppositories and can bind and neutralise BSP, in the blood or in tissue fluid, freely circulating or bound to factor H, Should there be a thus far non-proven protective function of the factor H complex against the alternative path of complement activation, this is inhibited and the tumor cells can be attacked by the immune system. Further, the angiogenic effect of BSP is inhibited.

For binding to the complex of factor H and BSP, the antibody must recognise epitopes of BSP which are not masked by the binding partner. The production of such antibodies has previously not been possible. The invention makes available such antibodies, because the antibodies are directed against an isoform of the folded bone sialoprotein (BSP) and bind to epitopes which are formed only by a folded bone sialoprotein from tumor cells, the glycosylations of which are modified or incomplete or missing in the region of the amino acids 120 to 135 (with signal sequence), including the amino acid sequence TGLAA (SEQ ID NO:15) or YTGLAA (SEQ ID NO:16), in comparison to the normal bone sialoprotein from bones. Normally there cannot be attained specific antibodies against post-translational or complex sugar structures on proteins, since such sugar structures are added in the same manner and form to many different proteins. Correspondingly, antibodies react against certain sugar structures with many different proteins and are then considered as a rule to be non-specific and of no value. This is different with bone sialoprotein from tumor cells. The altered or missing sugar structure brings about a different folding of the bone sialoprotein and creates new epitopes in which there are involved both amino acids or peptide structure and also the many remaining sugar residues. These epitopes are however characteristic for BSP from degenerate tumor cells.

Antibodies against these epitopes can be produced with a BSP, altered chemically or naturally in its glycosylation, as antigen and if applicable through purification or absorption to the isoform of the bone BSP. Preferably the antibodies are produced with the employment of BSP from tumor cells as antigen. Since BSP from tumor cells can be isolated in sufficient quantities only with difficulty, the genetically engineered expression of BSP modified in its glycosylation in tumor cells is the method of choice. It has also been found that some patients have in the bone material BSP modified in its glycosylation. This means that these patients, mostly very old and suffering from serious osteoporosis, produce a BSP which at least in part is not normally glycosylated. This BSP also is suitable in principle as an antigen for the obtaining of the antibodies in accordance with the invention. The isolation of the partially glycosylated isoform, which is comparable to the tumor isoform of the BSP, can be carried out analogously to described procedures (Karmatschek M et al., *Improved purification of human bone sialoprotein and development of a homologous radioimmunoassay*, in Clin. Chem. 1997, 43(11), 2076-82).

The antibodies can be produced in mice, guinea pigs, rabbits, dogs, goats, pigs, humans, donkeys or horses, but also in all mammals. Particularly preferred is the immunisation of birds, in particular chicken, since here due to the large evolutionary differences, antibodies against the tumor isoform of BSP can be obtained particularly easily. Further, the presence of IgY antibodies does not lead to an activation of the complement system, which could be problematic due to the possible binding between factor H and BSP. The antibodies in accordance with the invention recognise the tumor isoform of BSP in the bonding with factor H.

Thus, subjects of the invention are isoforms of BSP, particular antibodies against the isoforms produced by tumors, and their use for antibody therapy or also for immune scintigraphy. As side effects, which are brought about by anti-BSP antibodies, there come in question: direct and indirect damage of the bones and dentin through activation of the immune system against the bone matrix and bone cells and/or direct destruction, in the employment of conjugates of the antibody with cell poisons or radio isotopes. Further, an immune scintigraphy is inconceivable with anti-BSP antibodies which bind to the bone matrix. The matrix would be radioactively marked and the localisation of tumors would be impossible. The antibodies specific for human BSP are suitable in a particular manner for tumor therapy and localisation, since they do not bind or bind to only a slight extent to the bone matrix or to BSP producing cells of the skeleton and the dentin.

In a particularly preferred application of the invention there are put to use for tumor therapy antibodies which are specific for tumor BSP and additionally recognise BSP in the complex with factor H. Such antibodies are made available by the invention. After application of such specific antibodies in tumor patients, free tumor BSP and tumor BSP bonded to factor H, in the blood and in tissue fluid, is marked and therewith the protection against complement activation removed. Thus, tumor cells are specifically marked for destruction by the immune system (e.g. through classical activation of the complement cascade) and there are avoided side effects such as e.g. through activation of the immune system against the bone matrix or the dentin.

For the tumor therapy and immune scintigraphy made possible by means of the invention there can be employed by way of example polyclonal antibodies which can be produced by immunisation of chickens with recombinant BSP or BSP, modified in its glycosylation, isolated from bones. The antibodies are then isolated in known manner from the egg yolk and purified by affinity chromatography.

In a further application of the invention, human polyclonal anti-BSP antibodies are isolated from the eggs of transgenic chickens having humanised immune system.

Likewise suitable are monoclonal antibodies from the mouse or the chicken, which fulfil the above-described conditions and which can be obtained by means of screening. In a specific application of the patent there are employed for this purpose the monoclonal cell lines described by way of example. Further suitable are Fab fragments obtained through fragments of antibodies, e.g. proteolytically or by genetic engineering.

For the tumor therapy the above-described antibodies or antibody fragments are further suitable, in conjugation with cell poisons and radioisotopes, for the direct destruction of tumor cells after binding to BSP on the cell surface.

Particularly suitable are humanised poly- and monoclonal antibodies which recognise BSP in the complex with factor H and do not bind to BSP in the bone matrix. With the application of antibodies of the mouse and of the chicken there is however a particular therapeutic effect to be expected through formation of human anti-mouse antibodies (HAMA) or anti-chicken antibodies (HACA). HAMAs and HACAs can induce and strengthen an immune response of the organism to the tumor antigen. In the determination of tumor markers there arise, however, interferences with the HAMAs and HACAs which disrupt in vitro measuring methods. In this manner there are produced falsely high measurement values for tumor marker. This appears after immune scintigraphy or immune therapy with appropriate antibodies, so that a correct tumor marker determination in vitro can be effected only after absorption of the HAMAs or HACAs.

These effects can be suppressed through the employment of humanised antibodies. Polyclonal humanised anti-BSP antibodies can for example be obtained by immunisation of transgenic chickens with BSP, for which chickens in the embryonic stem cells the gene region for the chicken-specific Fc part of the immunoglobulin (IgY) is exchanged for a human specific one (U.S. Pat. No. 5,340,740; U.S. Pat. No. 5,656,479). The humanised antibodies are then deposited in eggs of the chickens and can be isolated from the egg yolk (Mohammed S. M. et al., Deposition of genetically engineered human antibodies into the egg yolk of hens. Immunotechnology, 1998, 4:115-125).

For the production of humanised monoclonal antibodies there may be obtained hybridoma cells of the mouse or the chicken with suitable anti-BSP antibodies, in accordance with standard methods, and from the genetic material contained in these cells humanised antibodies can be developed through recombination (U.S. Pat. No. 5,585,089; U.S. Pat. No. 5,565,332; U.S. Pat. No. 5,225,539; U.S. Pat. No. 5,693,761; U.S. Pat. No. 5,585,089; U.S. Pat. No. 5,530,101).

The BSP can be put to use with the entire sequence SEQ ID No. 1 or the part sequence ID No. 2, in its entirety or with its specific epitopes for the generation of antibodies.

Preferred BSP fragments for the production of specific antibodies are:

SEQ ID NO: 1
X-YTGLAAIQLPKKAGD-Z

SEQ ID NO: 2
X-FSMKNLHRRVKIEDSEENGVFKYRPRYYLYKHAYFYPHLKRFPVQGSS

DSSEENGDDSSEEEEEEEETSNEGENNEESNEDEDSEAENTTLSATTLGY

GEDATPGTGYTGLAAIQLPKKAGDITNKATKEKESDEEEEEEEEGNENEE

SEAEVDENEQGINGTSTNSTEAENGNGSSGVDNGEEGEEESVTGANAEGT

TETGGQGKGTSKTTTSPNGGFEPTTPPQVYRTTSPPFGKTTTVEYEGEYE

YTYDNGYEIYESENGEPRGDNYRAYEGEYSYFKGQGYDGYDGQNYYHHQ-

Z wherein the marked T is not or is incompletely glycosylated, or is glycosylated in another form, and X and Z stand for amino acid or peptide residues of up to 30 amino acids. In SEQ ID No. 2 the following variations may be present: at position 179 Gly→Val; position 252 Val→Ala; position 254 Glu→Asp; position 279 Asp→Gly.

For the production of the antibodies the peptides, which are normally not immunogenic, are coupled to the carrier protein KLH (keyhole limpet hemocyanin). This coupling can be effected through NBS (N-maleimidobenzoyl-N-hydroxysuccinimide ester) via a cysteine added terminally in the peptide, or directly by means of carbodiimide.

The antibodies are obtained with conventional processes through immunisation preferably of chickens, rabbits, mice, guinea pigs etc. There can be put to use also molecular biological processes, such as the recombinant production of the antibodies. The antibodies are then purified and galenically prepared. There may also be put to use cell preparations, cell extracts and in particular membrane isolates from over-expressing artificially transfected BSP expressing cells for the generation of specific antibodies.

The medicaments in accordance with the invention can be administered in suitable galenical application forms, in particular lyophilised form, taken up by mannite or similar sugars, in sterile ampoules for dissolving in physiological salt solution and/or infusion solution for repeated individual injection and/or continuous infusion in quantities from 300 mg to 30 mg pure antibody or BSP ligand per therapy unit. Preferably the medicament in accordance with the invention is put to use in a galenical application form in which the medicament is administered systemically or locally in biocompatible microspheres and via aerosol, intravenous or subcutaneous application.

With various routine procedures it is possible to determine that the tumor cells, upon administration of agonists, which bind to the corresponding proteome molecules, react in an anti-apoptotic, adhesive, mitotic and chemotactic manner. The restriction of its conservation, adhesion, mitotis or migration is brought about through prior incubation with antagonists or antibodies.

In the employment of highly purified antibodies against BSP in cell cultures of BSP-expressing tumor cell lines it could be determined that in the case of in vitro models these are in a position to bring about the apoptisis of tumor cells. If one cultivates cell lines or removed tumor cells with the employment of conventional cell culture processes, their survival time in vitro is strongly reduced through the addition of BSP antibodies, if BSP can be detected on their corresponding cell surface. Thereby there can be observed apoptosis of a great number of these cultivated cells. Also in the case of in vivo models one can, surprisingly, also determine a tumor cell regression through apoptosis.

Further, in experiments in the cell culture with tumor cells which express BSP, the use of specific BSP antibodies can initiate complement mediated cell lysis and also cellular mediated tumor cell lysis.

Since hairless mice and hairless rats have a deficient immune system, metastasising behaviour can investigated in a host body in a hairless mouse/rat model without the known immune reaction between species taking place and leading to rejection of the foreign cells. Hairless mice are inoculated, in a manner known per se, with tumor cells or tumor cell lines the BSP expression of which had been determined and the occurrence of metastasisation due to these cells monitored upon treatment with BSP antibodies and upon treatment with BSP ligands. Thereby it is surprisingly found that in the case of the BSP positive tumors found the formation of metastases is significantly restricted or prevented, because the administration of antibodies leads to a modulation of the tumor growth. Surprisingly it is likewise found that the preparations analysed by means of immunohistochemistry show a specific distribution of BSP and other tumor surface associated proteome clusters in the tumor and tissue surrounding the tumor. Through this, further possibilities for purposive attack have been recognised.

There is provided a broadening of the therapeutic concept through additionally employing antagonists in particular directed against further clusters of the tumor cell surface proteomes. A reinforcing of this effect can attained through a combination of BSP antibodies with antibodies, ligands or inhibitors which interact with (1) adhesion molecules, (2) membrane-associated proteases or (3) receptors which mediate chemotaxis, such as for example chemokine receptors, and (4) apoptosis inducing substances such as preferably antibodies or proteins/peptides which are obtained from natural or artificial peptide banks.

In order to confirm these findings, tumor cell lines can also be stably transfected with BSP. After injection of these cells (in the case of which BSP is over-expressed) into animals, such tumor cells settle preferentially in the bone matrix. Such modified cells therewith form in particular metastases in the bone tissue, on the basis of which the therapeutic principle can likewise be demonstrated.

The invention will be described in more detail below with reference to examples:

Example 1

Characterisation of Tumor and Bone Specific BSP Isoforms in Western Blot

Serum free supernatants of the human osteosarcoma cell lines UMR-108, MHH-ES 1 and of the breast cancer cell line MCF-7 (oestrogen receptor positive) and also of human BSP (K-BSP) purified from bones was separated by means of SDS-PAGE on a 10% gel under reducing and denaturing conditions and electrophoretically transferred to nitrocellulose. The membrane was incubated with the monoclonal mouse antibody. The detection of BSP was effected via an anti-mouse antibody of the goat coupled to peroxidase, and chemoluminescence detection on an X-ray film. The result is shown in FIG. 1. Molecular weight and path of the markers are indicated on the left side. The single and double arrowheads show the different behaviour of the bone/osteosarcoma BSP and MCF-7 BSP. The latter contains additionally a high molecular weight band (triple arrow) which is absent in the other tracks. BSP from one tumor cell line thus has a significantly higher molecular weight than BSP from bone and from osteosarcoma cell lines, whereby beyond this a second isoform with even higher molecular weight can be observed.

Example 2

Production of Polyclonal Antibodies by Means of Immunisation of Chickens with Bone BSP and BSP Peptide Part Structures Chickens and rabbits were immunised with BSP which was isolated from patients in accordance with the procedure described by Karmatschek et al. (1997).

From the egg yolks and the sera, polyclonal immunoglobulins were isolated and tested for binding against various peptide part structures of BSP in an ELISA process. Table 1 shows the results of this epitope mapping. Thereby, peptide part structures of the overall 317 amino acids long peptide sequence of preproBSP (including leader sequences) were chemically synthesised and bound to a microtitration plate and the antibodies incubated on the plate. The test for binding was effected after incubation with a conjugate of peroxidase with anti-IgY immunoglobulins or anti-rabbit-IgG immunoglobulins and subsequent enzyme reaction through transformation of a chromogene as substrate.

TABLE 1

Epitope mapping of the obtained anti-BSP IgG and IgY

| Position of the peptide part structure in the BSP (Position incl. Leader) | Amino acid sequence | Reaction strength ELISA | |
|---|---|---|---|
| | | IgY | Rabbit IgG |
| 112-123 (SEQ ID NO: 3) | LeuGlyTyrGlyGluAspAlaThrProGlyThrGly | − | ? |
| 216-227 (SEQ ID NO: 4) | GluThrGlyGlyGlnGlyLysGlyThrSerLysThr | − | ? |
| 300-311 (SEQ ID NO: 5) | PheLysGlyGlnGlyTyrAspGlyTyrAspGlyGln | − | ? |
| 130-144 (SEQ ID NO: 6) | IleGlnLeuProLysLysAlaGlyAspIleThrAsnLysAlaThr | +/− | + |
| 124-138 (SEQ ID NO: 7) | TyrThrGlyLeuAlaAlaIleGlnLeuProLysLysAlaGlyAsp | − | ++ |
| 137-151 (SEQ ID NO: 8) | GlyAspIleThrAsnLysAlaThrLysGluLysGluLysGlu-SerAspGlu | − | + |
| 280-317 (SEQ ID NO: 9) | SerGluAsnGlyGluProArgGlyAspAsnTyrArgAlaTyr-GluAspGluTyrSerTyrPheLysGlyGlnGlyTyrAspGly-TyrAspGlyGlnAsnTyrTyrHisHisGln | ++ | + |
| Human bone BSP | | +++ | +++ |

The results show that the obtained chicken antibodies preferentially bind to the C-terminal sequence of BSP, whereas the rabbit antibodies bind over a greater region.

Further, polyclonal antibodies (A0001) were obtained by means of immunisation of rabbits with the peptide structure TyrThrGlyLeuAlaAlaIleGlnLeuProLysLysAlaGlyAsp (position 124-138) (SEQ ID NO:7) of BSP which preferentially react to this peptide part structure, but also specifically with human bone BSP.

Polyclonal antibodies (AK_tBSP), however, which were obtained through immunisation of rabbits with the peptide part structures ThrGlyLeuAlaAla (position 125-130) (SEQ ID NO: 15), for example TyrThrGlyLeuAlaAla (position 124-130) (SEQ ID NO: 16), that is after coupling to bovine thyreoglobulin as carrier, react with the synthetic peptide part structure, but not with human bone BSP. These antibodies, surprisingly, recognise exclusively BSP from tumor cells.

For the investigations there were further employed the polyclonal antibodies A002 (obtained from L. W. Fisher) and A003 (obtained from Dr. van Ryden). These antibodies were obtained after immunisation with the peptide part structures (SEQ ID NO: 11)
TyrGluSerGluAsnGlyGluProArgGlyAspAsnTyrArgAlaTyr GluAsp
or (SEQ ID NO: 12)
LeuLysArgPheProValGlnGlyGly.

The former peptide originated from the C-terminus of the BSP (positions 278-295) and contains the RGD (ArgGlyAsp) recognition sequence of the BSP for receptors of the integrin type. The latter peptide originated from the N-terminus of the BSP primary structure. Also these peptides preferentially recognised the respective part structures and reacted specifically with human bone BSP.

Example 3

Obtaining of Recombinant BSP from Breast Cancer Cells as Antigen

From the plasmid B6-5g (Fisher L. W. et al., *Human bone sialoprotein. Deduced protein sequence and chromosomal localisation*, in J. Biol. Chem., 1990, 265(4), 2347-51) the complete cDNA for human BSP (without signal peptide) was amplified by means of PCR and cloned in the episomal eucaryotic expression vector pCEP-Pu (Kohfeldt E et al., *Properties of the extracellular calcium binding module of the proteoglycan testican*, in FESS Lett. 1997, 414(3), 557-61). The primers were as follows:

(SEQ ID NO: 13)
Nhe I BSP (sense)
5'GCCCGCTAGCCTTCTCAATGAAAAATTTGCATCG-3'

(SEQ ID NO: 14)
Not I BSP (antisense):
5'-CAATGACTGCGGCCGCTCACTGGTGGTGGTAGTAATTC-3''

The Nhe I and Not I slicing sites introduced with the primers were necessary for the cloning in the expression vector PCEP-PU. This vector is moreover, for facilitating the protein purification, provided at the 5'-ends of the multiple cloning sites with various tags (e.g. His, Myc, G8T). These tags can be detached after purification of the protein with a protease (e.g. factor X or enterokinase). That the correct reading frame was kept to was checked by means of sequencing.

The expression constructs were introduced by means of liposome mediated stable transfection (FUGENE™ transfection reagent of the company Roche) inter alia into the following human cell lines:
the embryonic kidney cell line EBNA-293,
the osteosarcoma cell lines SAOS-2 and MG-63
the human breast cancer cell line MCF-7.

Figure 2:
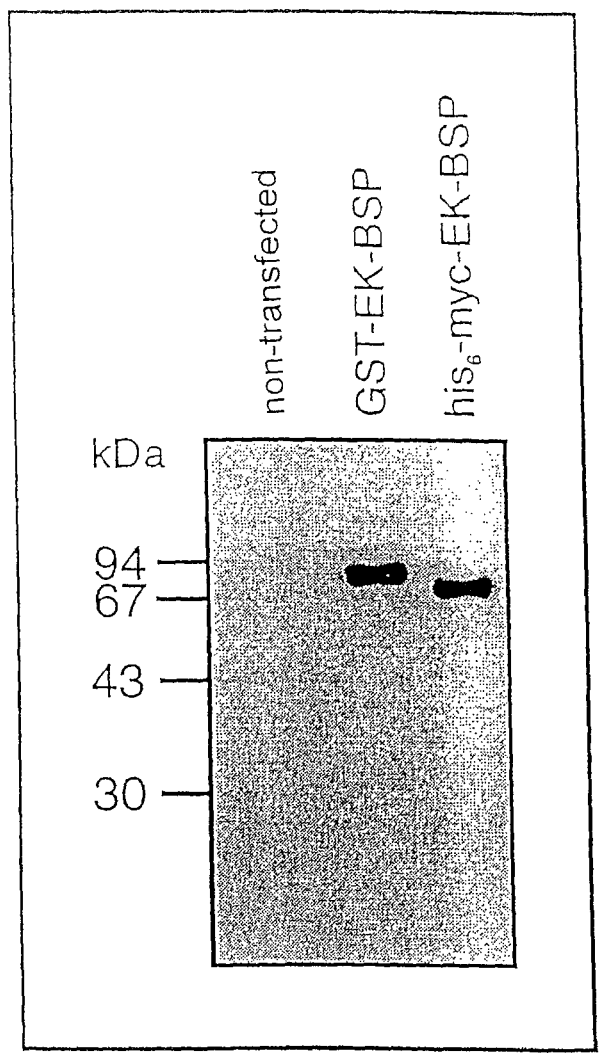
FIG. 2 a Western Blot of the cell culture supernatant of non-transfected EBNA-293 cells (negative control) and transfected EBNA-293 cells having the expression constructs GST-EK-BSP and his6-myc-EK-BSP with the employment of a monoclonal mouse anti-BSP antibody.
Figure 4A:
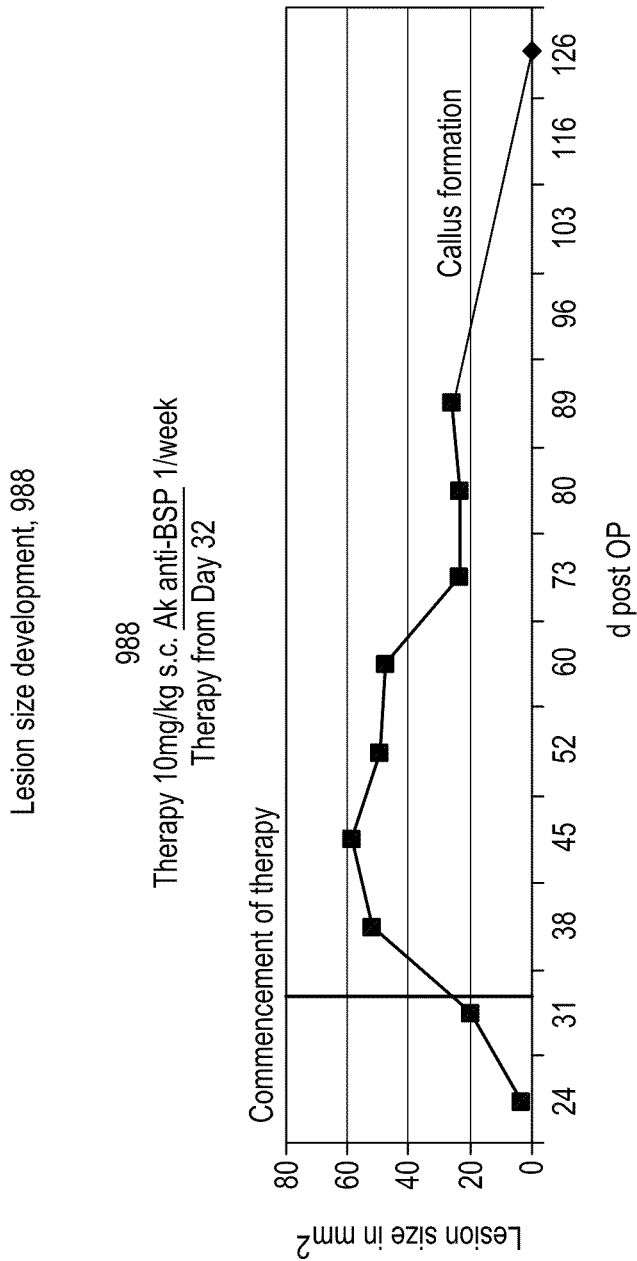
FIG. 4*a* a curve indicating lesion size in square millimeters of a bone metastasis in the tibia of rat 988 over the observation and therapy period.
Figure 4B:
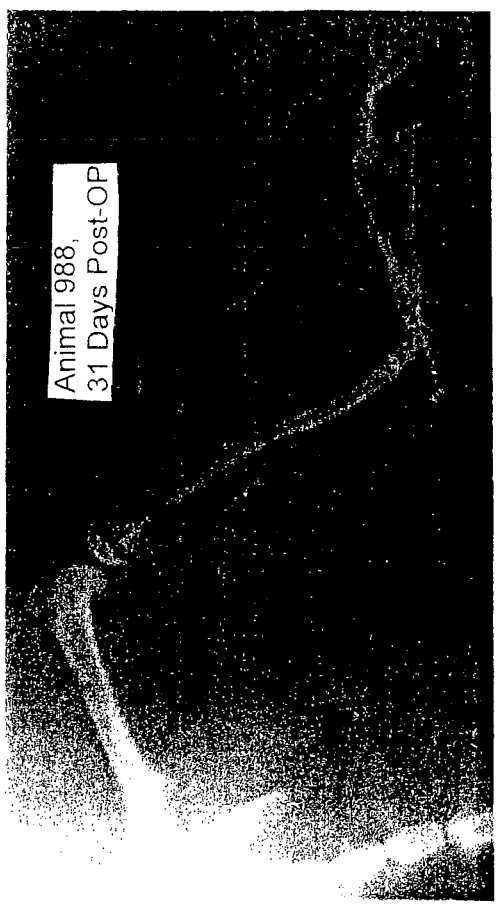
FIG. 4*b* an X-ray image 31 days post-OP of the lesion in the tibia, before the commencement of therapy.
Figure 4C:
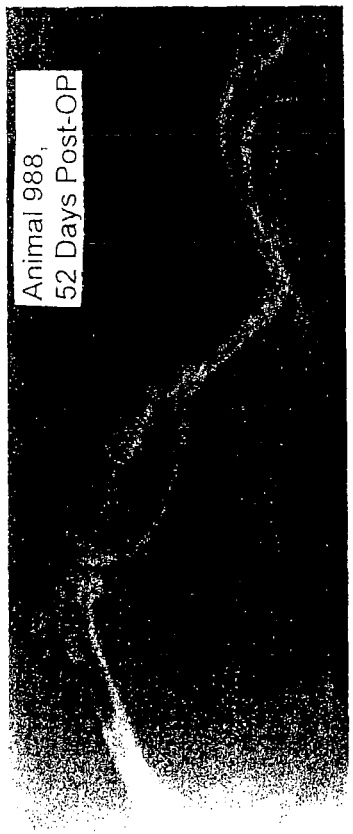
FIG. 4*c* an X-ray image 52 days post-OP of the lesion with still continuing lysis of the bone, after the commencement of therapy.
Figure 4D:
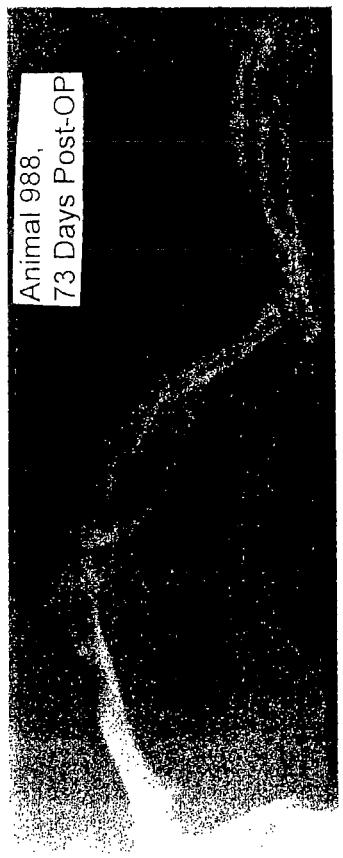
FIG. 4*d* X-ray 73 days post-OP of the regressing lesion.
Figure 4E:
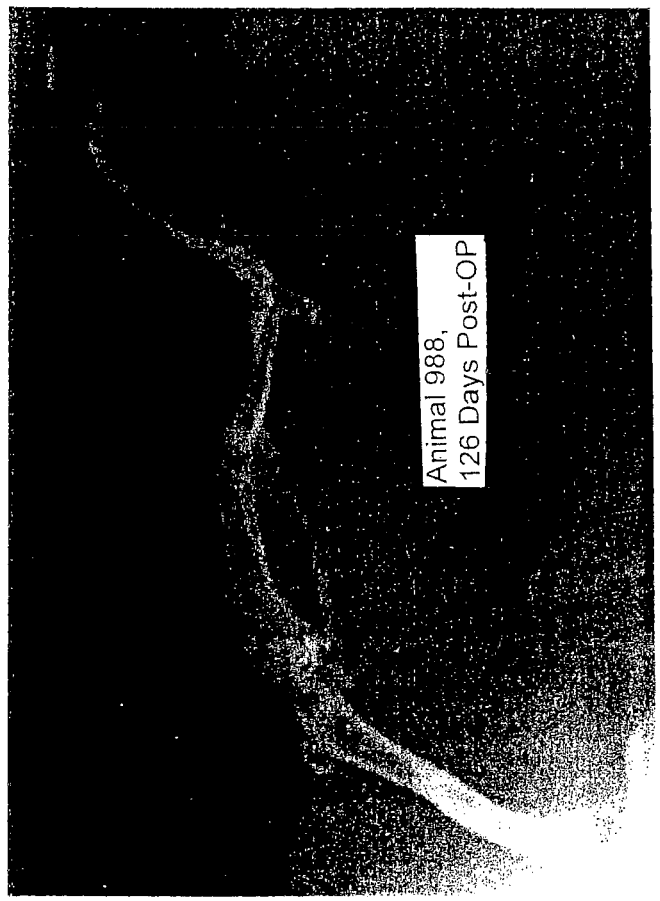
FIG. 4e X-ray 126 days post-OP of the healed lesion.
Figure 4F:
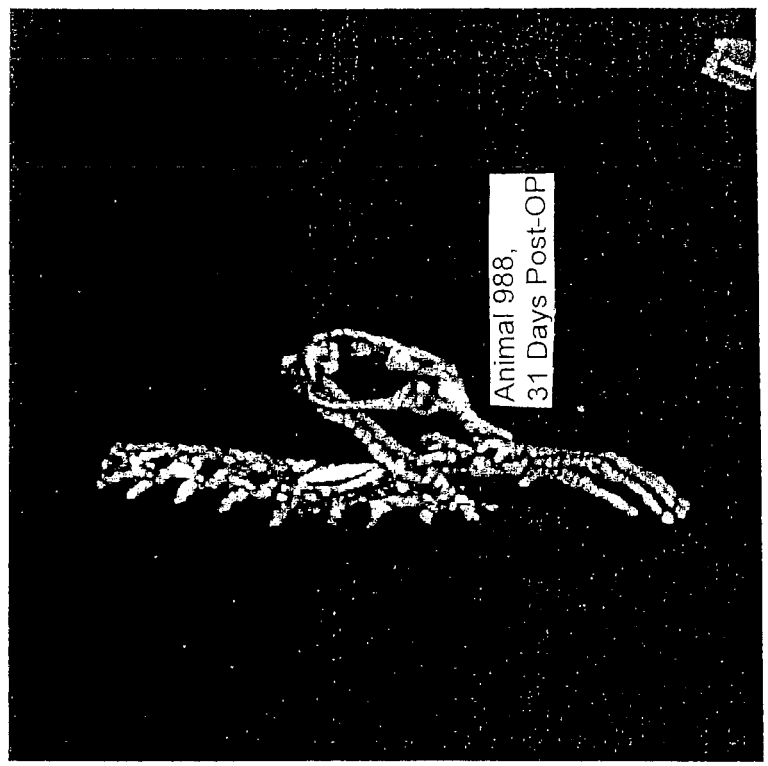
FIG. 4f CT reconstruction of the lesion 31 days post-OP.
Figure 4G:
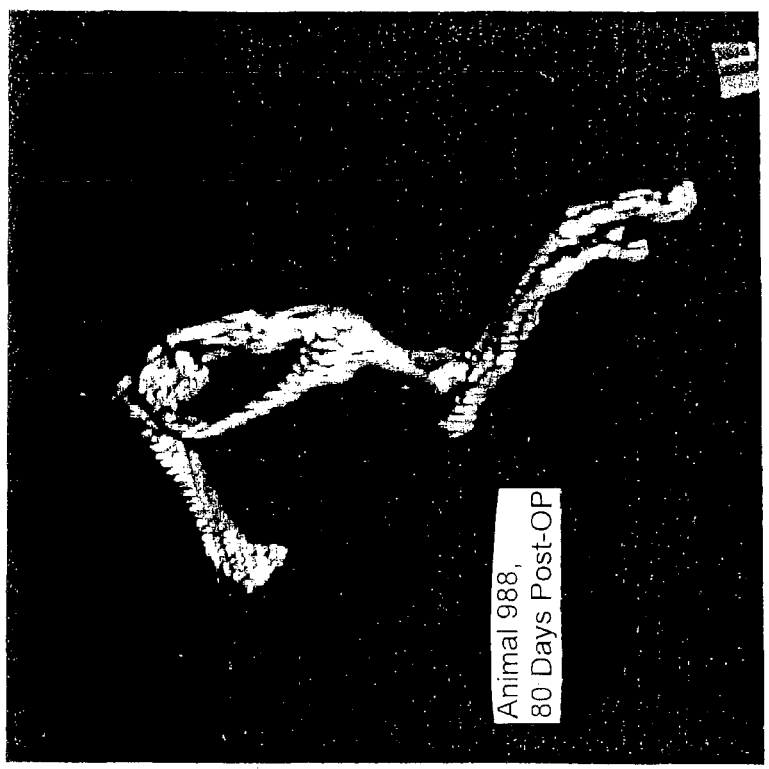
FIG. 4g CT reconstruction of the regressing lesion 80 days post-OP.

A recombinant expression was obtained only in MCF-7 and EBNA-293 cells (see FIG. 2). The osteosarcoma cell lines did not express even after repeated transfection attempts.

Example 4

Analysis of the Glycosylation of Recombinant BSP from Degenerate Cells and Bone BSP Transient cells were cultivated, 48 hours after transfection, for two days in serum-free medium. So that the proteins in the FCS did not make more difficult the purification of the recombinant BSP, BSP expressing cells were, after attainment of confluence, cultivated under serum free conditions. Under these conditions only EBNA-293 cells could survive longer than 2 to 4. The expression of the recombinant BSP was monitored through SDS-PAGE and immunoblots.

The investigation of serum-free cell culture supernatants yielded with all these cell lines a positive signal in the Western Blot, both with reference to BSP and also the presence of the various tags.

2.5 liter serum-free culture supernatant of the transfected MCF-7 cell line was purified via a Sepharose™ column and there was obtained therefrom 250 µg homogeneous His-myc-EK-BSP. The so purified expression product was partially glyglosylated, however had no glycosylation at threonin 125, that is the threonin in the BSP sequence YT$^{125}$LPAA (SEQ ID NO:17).

For the glycoanalysis the N-glycanes were enzymatically separated from the recombinant BSP (rBSP) or the bone BSP with the peptide N-glycosidase F (PNGase F, Roche). The enzyme brought about a cataylytic splitting of all N-glycane types from the asparagines. For the digestion, 20 to 200 µg BSP was precipitated with ethanol and the precipitant pellet incubated in 1% SDS, β-mercaptoethanol, 0.1 M EDTA for 30 minutes at room temperature with an excess of enzyme. There followed a digestion with N-glycosidase F overnight at 37° C. For de-salting the N-glycane solution the digestion was given via a 150 mg carbon column (carbograph SPE, Alltech) and the N-glycanes eluted with 25% aCN in 0.05% TFA.

The O-glycanes were sliced from the BSP by means of water-free hydrazinolysis using a kit (Oglycan release kit, Glyco). For this purpose, approximately 200 µg salt free BSP was lyophilised for 24 hours, had 50 µl hydrazine reagent added thereto under argon protective gas, dissolved and incubated for 5 hours at 60° C. The hydrazine was drawn off under vacuum. There followed a Re—N-acetylisation of the N-acetyl groups with acetic acid anhydrid.

The N- and O-glycanes were marked with the fluorescence dye 2-aminobenzamide (Fluka) and the 2-AB marked oligosaccharides digested sequentially with specific terminal glycosidases and analysed by means of MALDI-TOF mass spectrometry.
Discussion of the Analysis The amino acid sequence of human BSP contains four potential N-glycosylation sites at the positions 88 (NTT), 161 (NGT), 166 (NST) and 174 (NGS).

For O-glycosylation there is known no comparable consensus sequence. All identified N-glycane structures could be found both on the BSP isolated from bones and on the recombinant EBNA-293 BSP. There were however differences in the percentage proportion of the respective structures in the total N-glycanes. Thus, the main proportion of the BSP N-glycanes in bones was of triantenary structures (58%) and in the EBNA cell line of tetraantenary structures (48%).

For localisation of the O-glycosylation sites of recombinant BSP, the O-glycanes were removed by means of sequential digestion of the protein with neuraminidase, β-galactosidase and β-N-actylhexosaminidase, down to the core-GalNAc. The partially deglycosylated protein was then split by treatment with trypsin and V8 protease into peptide fragments. By means of MALDA-TOF mass spectrometry the masses of the peptides were determined and a part of the peptides sequenced by means of PSD-MALDI-TOF mass spectrometry. With this method, eight O-glycosylation sites of the recombinant BSP could be determined, 5 on the peptide 211-229 (TTTSP . . . QVYR) of SEQ ID NO:2 and a maximum of 3 on the peptide between AS 120 and AS 135 having the sequence TGLAA (SEQ ID NO:15). Of these, in the recombinant BSP, the threonines in the sequence DATPGTG (SEQ ID NO:18) are O-glycosylated. With bone BSP there was effected a third O-glycosylation. With recombinant BSP no third glycosylation site is present. Probably, this glycosylation site lies on the TGLAA-BSP part structure.

Example 5

Production of Anti-BSP IgY from Egg Yolks

For the purification of greater quantities of anti-BSP IgY for therapy and immune scintigraphy there are described various processes. The process of Akita and Nakai (Akita E. M. et al., Comparison of four purification methods for the production of immunoglobulins from eggs laid by hens immunised with an enterotoxigenetic E. coli strain, in J Immunol Methods. 1993, 160(2), 207-14) is preferentially used.

For the egg production there is used a highly productive species such as "Lohmann White" or "Lohmann Brown" with a productivity of 4.5 eggs per week and a production of over 10 mg specific IgY per yolk. The immunisation was effected with BSP antigen isolated from human bones, or recombinant, in Freund's Adjuvant, whereby after a basic immunisation with ca. 0.1 mg BSP, booster injections where given every six weeks. Normally ca. 30% of these chickens do not react to the immunisation. The eggs were externally disinfected with peracetic acid, then broken and yolk separated from egg white. The yolks were then whisked with 5 to 10 times volume ice cold distilled water between pH 5 and 5.2 and incubated at 2 to 5° C. over 2 to 6 hours. Thereby there sediments out the yolk granulata which are substantially of lipoproteins. The aqueous supernatant was then filtered clear through filter paper (e.g. Whatman No. 1).

From this supernatant, the anti-BSP IgY can be homogenously purified directly or via affinity chromatography. There was chemically covalently bonded, through a Sepharose 4B column, activated with cyanogen bromide, BSP isolated from human bones or from culture supernatants of recombinant human cell lines. For bonding 1 g IgY there is needed 0.5 g immobilised BSP (covalently bonded to ca. 5 ml Sepharose™).

The bonded IgY is eluted via an acid gradient and thereafter the solution neutralised. This solution must then be desalted and the antibodies concentrated, which is possible on an large scale in the crossflow method (e.g. Amicon™, spiral filter SY 100 with a yield of 100,000 Dalton).

Example 6

Isolation of Anti-BSP IgY which is Bonded to the BSP Factor H Complex

The slight reaction of the polyclonal chicken antibody with BSP in the bone matrix can be excluded through selection of those antibodies which react with BSP in the complex with factor H. For this purpose there is chemically covalently bonded through cyanogen bromide activated Sepharose 4B either factor H or BSP isolated from bones or genetically engineered, and thereafter so much BSP or factor H applied to the column and bonded that all ligands in the matrix are complexed with the partner. Filtered yolk extract is then applied to this affinity column and as in Example 4 there is now obtained that fraction of antibodies which specifically bonds to the free epitope in the BSP-factor H complex.

Example 7

Production of Human Anti-BSP Antibodies in Transgenic Chickens

Anti-BSP IgY has in human therapy or diagnosis some weaknesses. Some side effects such as foreign protein reactions are to be expected and the biological half-life amounts in comparison to human antibodies only to 12 to 24 hours. IgY does not activate the complement system.

Human antibodies against BSP can be produced in particular transgenic chickens, in which by means of gene targeting the constant region for avian immunoglobulin in the genes responsible for antibody formation has been exchanged by the constant region for human immunoglobulin. Suitable chicken stem cells and vector systems are described in U.S. Pat. Nos. 5,340,740, 5,656,479 and 5,464,764. After immunisation with BSP, such chickens react with the production of human antibodies in the egg.

Example 8

Immunoblot Analysis of the Expression of BSP in Human Breast Cancer Cell Lines

The tumor cell lines MDA-MB-231 (breast cancer cell line, oestrogen receptor negative) MCF-7 (breast cancer cell line, oestrogen receptor positive) and T-47-D (breast cancer cell line, oestrogen receptor positive) were extracted with immune precipitation buffer and BSP precipitated with the polyclonal antibody mixture A0001 of rabbits against human BSP. The precipitates were applied, after denaturing, to SDS gels, the electrophoresis was carried out and the proteins transferred to nitrocellulose membranes. Thereafter there followed an immune colouring with the anti-BSP rabbit antiserum A001 and a monoclonal mouse-anti-BSP antibody (BSP 1.2), whereby there was employed as second antibody peroxydase conjugates of antibodies of the goat against rabbit IgG and against mouse IgG. In both blots A and B the bands of the immune precipitated BSP can be clearly recognized at 70000 Dalton.

In order to show the presence or absence of BSP on the cell surface of tumor cells, the cell surfaces of the breast cancer cell lines MDA-MB-231 and MCF-7 were biotinylated, extracted with immune precipitation buffer and BSP precipitated with the polyclonal antibody mixture A0001 of the rabbit against human BSP. The precipitates were, after denaturing, applied to SDS gels, the electrophoresis carried out and the proteins applied to a nitrocellulose membrane. Biotinylated proteins on this membrane were then demonstrated with a conjugate of peroxydase and streptavidine with the ECL system (Amersham).

Human breast cancer cells of the lines T-47-D and MDA-MB-231 were marked immunofluorescently, both with and without prior permeablisation, with an anti-pig-BSP antibody from rabbit and an anti-rabbit antibody of the goat conjugated with fluorescene. Fluorescently marked BSP can be recognised in both cell lines after permeablisation. Only in the T-47-D cells could BSP be demonstrated by immunofluorescence also without permeabalisation.

Example 9

Detection of BSP Expression in Tumor Cells Via RT-PCR

From the tumor cell lines MDA-MB-231 (breast cancer cell line, oestrogen receptor negative), MCF-7 (breast cancer cell line, oestrogen receptor positive) and T-47-D (breast cancer cell line, oestrogen receptor positive) and human fibroblasts (HGF) as control cells, there was isolated mRNA, by reverse transcriptase the complementary cDNA was produced, and the BSP-cDNA amplified by means of PCR with BSP specific primers. The expression of BSP-mRNA was particularly high in the breast cancer cell line MCF-7, slight in the case of the MDA-MB-231 and T-47-D cells and not detectable in the control cell line.

Example 10

Production of Humanised Monoclonal Antibodies

The monoclonal antibody BSP 1.2 can, due to its specific binding to tumor BSP, be put to use for the therapy of primary tumors and metastases. Thereby, the antibody binds on BSP on the cell surface of certain tumor cells and stimulates the immune system to destroy the cells, e.g. via the activation of the complement cascade. Similarly, there can be put to use also the polyclonal or monoclonal anti-BSP IgY for therapy. When this antibody is used, the human immune system reacts with the formation of its own antibodies—human anti-mouse-IgG antibodies (HAMAs) or human anti-chicken-IgY antibodies (HACAs). HAMAs and HACAs can induce or strengthen an immune response of the organism to the tumor antigen. In the determination of tumor markers there arises, however, interferences with the HAMAs and HACAs which disrupt in vitro measurement methods. In this way there arises falsely high measurement values for tumor marker.

Thus, humanised monoclonal antibodies are particularly suitable for the therapy and immune scintigraphy. A plurality of methods have been described how one derives appropriately humanised antibodies from the hybridoma cell lines, which produce monoclonal anti-BSP antibodies.

Example 11

Conjugates of Anti-BSP Antibodies with Cell Poisons and Radioisotopes

In a further application of the invention there may be chemically covalently bonded with the anti-BSP antibodies or their Fab fragments cell poisons and radioisotopes. Antibodies marked with radioisotopes such as iodine 125 or iodine 131 are suitable with the application of smaller quantities for tumor localisation via immune scintigraphy and with the application of greater quantities for the direct destruction of the tumors. Such chemical conjugates can be produced for example by iodisation of the antibody with iodine 125 or 131 (Garvey, J. S et al., Methods in Immunology. 3$^{rd}$ ed., W. A. Benjamin Publ., 177, 171-182). An overview of suitable methods for radio immune therapy and immune scintigraphy is found in Vuillez, Radioimmunotargeting: diagnosis and therapeutic use, in Bull Cancer. 2000, 87(11), 813-27.

Example 12

Therapy of Tumors with Expression of BSP on the Cell Surface

It was first determined from biopsy material whether BSP was expressed on the surface of the tumor cells. Patients for whom BSP can be detected on the surface of the tumor cells can be considered for therapy with anti-BSP antibodies of the chicken, the mouse, the correspondingly humanised antibodies and with conjugates of these antibodies with cell poisons or radioisotopes.

The treatment of tumors with therapeutic antibodies which are directed against tumor markers expressed on the cell surface is state of the art. Thus, with the humanised antibody herceptin, against the receptor for the human epithelial growth factor, breast cancer can be successfully treated, even in the metastasising form, in ca. 25% of those affected (Hotaling T E et al., The humanized anti-HER2 antibody rhuMAb HER2 mediates antibody dependent cell-mediated cytotoxicity via FcgR III [abstract]. Proc Annu Meet Am Assoc Cancer Res 1996; 37:47; Pegram M D et al., Antibody dependent cell-mediated cytotoxicity in breast cancer patients in Phase III clinical trials of a humanized anti-HER2 antibody [abstract]. Proc Am Assoc Cancer Res 1997; 38:602.

Similarly as with herceptin, the appropriate anti-BSP antibody can be applied as an infusion, e.g. as a 90 minute infusion in the first application and later as a 30 minute infusion. The frequency of the infusions and the quantity of the antibodies are determined in accordance with the half-life of the antibodies in the blood (ca. 6 days with a humanised antibody and less than 24 hours with a chicken antibody) and the body weight.

Example 13

Therapy of Tumors by Means of Neutralisation of Free BSP, not Bonded to Cells, and of the BSP-Factor H Complex With the methods described above it was determined that the tumor cells of the patient express BSP which cannot be detected on the cell surface. In the case of these tumors it can be assumed that the cells give out BSP into the blood or the tissue fluid and e.g. through binding of factor H use this for the inactivation of the alternative path of the complement cascade or for migration into bone tissues. A further possible indicator for this tumor type are increased concentrations of the BSP in the blood serum (>20 ng/mL serum). In these cases anti-BSP antibodies can be put to use for the neutralisation of the free tumor BSP or the tumor BSP in complexes with factor H. The dose can then be set with regard to the quantity of the BSP present free in the serum and in the tissue fluid. For the therapy, there can be considered anti-BSP antibodies of the chicken, of the mouse and humanised anti-BSP antibodies, which can recognize the free BSP epitope in the complex with factor H. There can also be considered Fab fragments of these antibodies, which can be prepared in accordance with a standard procedure by means of proteolytic digestion (Garvey, J. S et al., Methods in Immunology. 3$^{rd}$ ed., W. A. Benjamin Publ., 1977, 256-266). Also genetically engineered Fab fragments, derived from the above anti-BSP antibodies, come into consideration for such a therapy.

The invention thus makes available antibodies against the human bone sialoprotein (hBSP) which bind specifically only epitopes of hBSP of tumor cells, since tumor hBSP contains no post-translational O-glycosylation in the region of the amino acids 120 to 135 (SWISSPROT: SIAL_HUMAN, Acc. No. P21815, without signal sequence) containing the amino acids TGLAA (SEQ ID NO:15). Differently from the normal hBSP from bones. The antibodies can recognize tumorgenic serum hBSP in the complex with the complement factor H and thus constitute a diagnostic and therapeutically valuable instrument.

Example 14

Production of Specific Antibodies Against BSP or Other Clusters of the Tumor Cell Surface Proteomes For the production of specific antibodies against the said proteins it has surprisingly been found that along with the use of complete molecules also specific amino acid sequences of epitopes are suitable particularly for the immunisation when the synthesised peptides are coupled to carrier molecules in accordance with the usual methods and injected into mice. Further, also multiple antigenic peptides (sequences see above) are suitable which are bonded to larger molecules by means of lysine, or BSP transfected cell lines, in order to produce these antibodies. As a further method, the employment of immunogenes of stable transfected BSP-expressing cells has proved itself surprisingly well, whereby membrane isolates, cell extracts with complete or fragmented receptors or also lyophilisated overall preparations are used.

Mice (Type NZW×NZB) were put to use for production of monoclonal antibodies, which was carried out with the routine methods of Immundiagnostik AG and IPF PharmaCeuticals GmbH. The antibodies monitored by means of Western Blot and ELISA can, after high level purification, be put to use for the mentioned diagnostic and therapeutic purposes.

Example 15

Initiation of Apoptosis by Means of BSP Specific Antibodies in BSP Expressing Cell Lines Expression analysis of various cell lines have inter alia shown that prostate tumor cell lines and also breast tumor cell lines express BSP. This expression was carried out on the mRNA level by means of RT-PCR and on the protein level by means of Western Blot and FACS analysis. A treatment of these BSP expressing tumor cell lines with BSP specific antibodies has lead in cultivated cells to programmed cell death, which should be detected inter alia by means of through-flow cytometry.

Example 16

Reduction of Bone Metastases in the Animal Model

After the application of BSP expressing tumor cell lines in immune deficient hairless mice/hairless rats bone metastasisation regularly occurs. With the simultaneous administration of the BSP specific antibody there occurred, surprisingly, a significant reduction of the formation of manifest bone metastases, which could be proven through histological analysis of the tissue.

1. Material and Methodology

Our animal model involved injection of breast cancer cells and subsequent therapy of the lytic lesions arising with anti-BSP antibodies, which represented a mixture of polyclonal IgY antibodies of the chicken with predominant specificity for human BSP from tumor cells, which also quantitatively bind hBSP in human serum in the presence of factor H, and which mainly bind to an epitope in the region of amino acids 120 to 135 of the hBSP, whereby the post-translational glycosylation in this region is in the case of hBSP from tumor cells altered in comparison with natural BSP from bones.

There were injected MDA-MB 231-cells (ATCC, HTB-26), which in a previous study with hairless mice have been applied intracardially (T. A. Guise, 1997; PTH-rP and Bone metastases; American Cancer society). The cell line was obtained from a metastasising human adenocarcinoma; further it has no oestrogen receptors. In our case, it was marked with green fluorescent protein (GFP) which facilitated the identification of the cells in the histological preparation. As experimental animals there were used hairless rats of an age from 6 to 8 weeks (RNU, Charles River Breeding, Sulzfeld, Germany) which have reduced immune competency, so that the injected human cells are not recognised as such and combated. Our preparatory investigations with various cell quantities, with male and female animals, showed that in the case of male rats the metastases were visible in the form of lytic lesions following injection of $10^5$ MDA-MB 231 cells, after about one month.

The cells ($1 \times 10^5$ in PBS puffer) were injected intraarterially into the *A. femoralis* (0.2 ml; n=8). For this purpose a side branch of this vessel was cannulised and after injection bound off, in order to prevent exit of the introduced cells. The animal compensated the loss of the vessel by means of collateral formation without difficulty. The cancer cells then entered with the blood into the fine branchings of the supplying branches of the femur, tibia and fibula. Here, in the terminal flow path, there takes place extravasation and subsequent adhesion of the cells to the bone matrix. It is probably here also that the interaction with BSP takes place.

The subsequent monitoring of metastases growth was effected on a ten day basis with conventional X-ray images, anterior-posterior and posterior-anterior, with the animal anaesthatised with ether. An approximate quantification was carried out by means of measurement of lesion in terms of the length and width of its extent.

After two positive X-ray checks, the animals were treated with anti-BSP-Ak or standard. The therapy was effected with the described animals once per week subcutaneously in a concentration of 10 mg/kg body weight.

The follow-up observation of the animals was further effected by means of computer tomography and histology (not yet completed). The CT allowed a three-dimensional reconstruction of the bone and of the defect, and an exact measurement of the lesion size. After the observation time the animals were killed and investigated histologically. By means of the marking with GFP the cells are visible under UV light in the bone section preparation. Further, histologically more direct information of the proceeding transformation of the bone tissue could be made.

2. Results

Figure 5B:
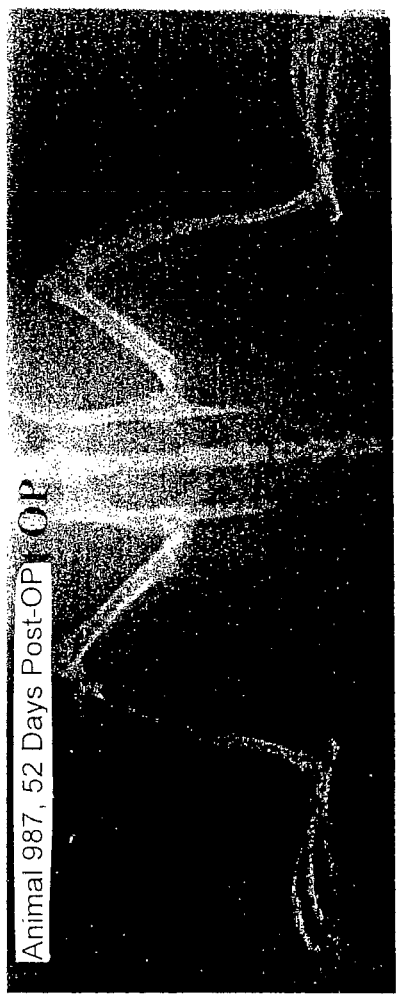
FIG. 5b X-ray 52 days post-OP of the lesion on the distal femur.
Figure 5C:
FIG. 5c X-ray 96 days post-OP from the regressing lesion and the callus formation.

The results are documented by way of example in the accompanying series of FIGS. 4 and 5. The animals were observed after the operation for more than three months by X-rays (Siemens Opti 150/30/50 HC-100). In the development of the curves attention is to be given to the fact that the area indications of the lesion size in $mm^2$, indicated on the ordinate, are different for the two indicated animals. Overall, eight animals were treated.

Animals 987 and 988 (see the Figures) were treated subcutaneously with the anti-BSP-Ak (10 mg/kg) once per week. The overall duration of the treatment was ca. 50 days. The therapy was commenced after 2 or 3 positive X-ray checks. In the case of animal 987 this corresponds to day 46 after the operation, and in the case of animal 988 to the $32^{nd}$ postoperative day.

A rapid lesion size increase from the $24^{th}$ postoperative day was in the case of animal 988 followed by a advancing lysis of the bone, which from day 38 led to a fracture in the middle third of the tibia. This took place after therapy had begun (from day 32). First healing tendencies show themselves from day 52 in the form of callus formation at the fracture site, and also the lesions on the proximal tibia and a distal femur became smaller. The outer bounderies of the lesions were initially sharply defined, later during the healing increasingly less sharply defined. The new formation of the bone took place starting from the outer perimeter towards the center of the lesion. From day 89 the lesion size could be quantified only with difficulty, since through the increasing callus formation the exact edges could no longer be recognised. After the $126^{th}$ day one can speak of a complete remission, which is shown by the accompanying image (complete disappearance of the X-ray recognisable lytic leasion). The three-dimensional CT reconstructions (Siemens Somato Plus 4, Volume Zoom) show the changes of the tibia lesion after 31 and 80 days post OP. There can be seen a clear increase of bone tissue.

Animal 987 was, after three positive X-ray findings, also treated with 10 mg/kg s.c. once per week from day 46. Here there appeared only a metastasis in the distal femur which already from the $89^{th}$ postoperative day (that is after 42 days of treatment) was healed.

Other animals were, under the same conditions, treated up to five times per week with 10 mg/kg s.c. and up to twice per week with 10 mg/kg i.v. There could be observed, however, an increase of size of the lesion during and after completion of the treatment, if during the treatment an immune reaction against the injected BSP antibodies was induced.

For comparison, animals were treated twice per week with alkylphosphorcholine Er-PC$_3$ with 40 µMol/kg i.v. which at this concentration allowed primary breast carcinoma to regress (positive control), but showed no effects in the case of bone metastases (Berger, M. R. et al., (1998) Erucylphosphocholine is the prototype of i.V. injectable alkylphosphocholines. Drugs of Today, 34 (Sppl. F), 73-81). Here, after the completion of the treatment, in the case of one animal no change was shown, by another even a deterioration of the situation (progression) in comparison to the beginning of treatment.

The subject of the present invention is thus a medicament containing antibodies or binding molecules such as aptamers against tumor specific BSP or other ligands for the same protein. Further, the employment of the proposed medicament application can be reinforced through the use of the following substances: antibodies, ligands or inhibitors which interact with adhesion molecules, membrane-associated proteases or receptors which mediate chemotaxis, for example chemokin receptors, and apoptosis inducing substances such as preferably antibodies or proteins/peptides which may be obtained from natural or artificial peptide banks. The medicament can be employed alone or in combination with the above-mentioned substances in particular for the therapy of tumor diseases, preferably their bone metastases.

The invention further relates to a method of therapy and the medical and commercial use of the said antibodies against BSP or other ligands for the same protein, or their combination with reinforcing antibodies or ligands or inhibitors which interact with adhesion molecules, membrane-associated proteases or receptors which mediate chemotaxis, such as for example chemokin receptors, and apoptosis inducing substances such as preferably antibodies or proteins/peptides which can be obtained from natural or artificial peptide banks, in order to suppress the cancer growth inclusive of metastasisation. The method is based on the determination that BSP can act on specific tumor cells through the disease-specific constellation of the expression. Primary and secondary tumors are, inter alia controlled in their migration and proliferation behaviour by BSP. From this there is provided the possibility of decisively hindering or completely suppressing cancer growth and tumor metastasisation by means of the said method/therapy.

The invention claimed is:

1. A method of treating and combating a tumor, or for treating metastases of said tumor, in which the metastases of said tumor preferentially settle in bone tissue, comprising
administering to a patient in need thereof a pharmaceutical composition comprising at least one antibody or an epitope binding fragment thereof, that specifically binds to an epitope from human bone sialoprotein, wherein the epitope comprises the amino acid sequence TGLAA (SEQ ID NO:15) or YTGLAA (SEQ ID NO:16).

2. The method according to claim 1, wherein the at least one antibody or epitope binding fragment thereof binds to bone sialoprotein naturally modified in its glycosylation.

3. The method according to claim 1, wherein the at least one antibody or epitope binding fragment thereof binds to bone sialoprotein from tumor cells and does not bind to bone sialoprotein from normal cells.

4. The method according to claim 1, wherein the at least one antibody or epitope binding fragment thereof binds to an epitope which is only presented on human bone sialoprotein from tumor cells, wherein post-translation glycosylation of the human bone sialoprotein from tumor cells corresponding to the region of amino acids 108 to 122 of SEQ ID NO:2 containing the amino acids TGLAA (SEQ ID NO:15) is modified or the region is incompletely glycosylated in comparison with normal bone sialoprotein from human bones.

5. The method according to claim 1, in which the at least one antibody is a humanized antibody.

6. The method of claim 1, in which the at least one antibody or epitope binding fragment thereof is incorporated into biocompatible microspheres.

7. The method according to claim 1, wherein the pharmaceutical composition further comprises a radionuclide.

8. The method according to claim 1, wherein the pharmaceutical composition further comprises an inducer of apoptosis.

9. The method according to claim 1, wherein the pharmaceutical composition further comprises an inhibitor of BSP activity.

10. The method of claim 1, in which the tumor is an osteophilic one selected from the group consisting of a prostate tumor, a breast tumor, a lung tumor, a kidney tumor, a thyroid tumor, a cancer of the blood system, a cancer of the lymphatic system, a tumor of the heart and circulatory system, a tumor of the nervous system, a tumor of the respiratory tract, a tumor of the digestive tract, a tumor of the endocrine system, a tumor of the skin, a tumor of the locomotory system and a tumor of the urogenital tract.

* * * * *